US012597522B2

(12) United States Patent
Heo et al.

(10) Patent No.: US 12,597,522 B2
(45) Date of Patent: Apr. 7, 2026

(54) METHOD AND SYSTEM FOR MANAGING PRESSURE ULCERS AND COMPUTING DEVICE FOR EXECUTING THE SAME

(71) Applicant: AJOU UNIVERSITY INDUSTRY-ACADEMIC COOPERATION FOUNDATION, Suwon-si (KR)

(72) Inventors: Jae Sung Heo, Seoul (KR); Sang Hyun Lim, Yongin-si (KR); Hyo Geun Rim, Seongnam-si (KR); Eun Sun Chung, Hwaseong-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 271 days.

(21) Appl. No.: 18/365,284

(22) Filed: Aug. 4, 2023

(65) Prior Publication Data

US 2024/0055136 A1    Feb. 15, 2024

(30) Foreign Application Priority Data

Aug. 12, 2022    (KR) ........................ 10-2022-0101524

(51) Int. Cl.
*G16H 50/30*    (2018.01)
*A61B 5/00*    (2006.01)
(Continued)

(52) U.S. Cl.
CPC ............. *G16H 50/30* (2018.01); *A61B 5/445* (2013.01); *A61B 5/447* (2013.01); *A61B 5/7289* (2013.01);
(Continued)

(58) Field of Classification Search
CPC ........ G16H 50/30; G16H 10/60; G16H 40/40; G16H 30/40; G16H 40/20; G16H 40/67;
(Continued)

(56) References Cited

U.S. PATENT DOCUMENTS

2005/0251415 A1* 11/2005 Pak ........................ G16H 40/67
705/2
2020/0193597 A1    6/2020 Fan et al.
2022/0192556 A1* 6/2022 Sankar .................. A61B 5/1116

FOREIGN PATENT DOCUMENTS

KR    10-2020-0111671 A    9/2020
KR    10-2020-0134702 A    12/2020
(Continued)

OTHER PUBLICATIONS

Feng, Haolin et al. "Optimizing outpatient appointment system using machine learning algorithms and scheduling rules: A prescriptive analytics framework." Expert Systems with Applications. vol. 102, Jul. 15, 2018, pp. 245-261 (Year: 2018).*
(Continued)

*Primary Examiner* — Linh Giang Le
(74) *Attorney, Agent, or Firm* — Sughrue Mion, PLLC

(57)    ABSTRACT

Disclosed are a method and system for managing pressure ulcers and computing device for executing the same. The computing device according to a disclosed embodiment is a computing device provided with one or more processors and a memory storing one or more programs executed by the one or more processors, the computing device including a pressure ulcer risk level evaluation module configured to acquire pressure ulcer risk factor information of a patient admitted to a hospital and calculate a pressure ulcer risk level of the corresponding patient based on the acquired pressure ulcer risk factor information, and a pressure ulcer prevention management module configured to schedule a pressure ulcer
(Continued)

100 prevention activity for a patient whose pressure ulcer risk level is equal to or higher than a predetermined threshold level.

17 Claims, 7 Drawing Sheets

(51) Int. Cl.
 *G16H 10/60* (2018.01)
 *G16H 40/40* (2018.01)
(52) U.S. Cl.
 CPC ............. *A61B 5/746* (2013.01); *G16H 10/60* (2018.01); *G16H 40/40* (2018.01)
(58) Field of Classification Search
 CPC ........ G16H 50/20; G16H 50/70; G16H 20/00; G16H 50/50; G16H 80/00; A61B 5/445; A61B 5/447; A61B 5/7289; A61B 5/746; A61B 5/7267; A61B 5/0077; A61B 5/0082; A61B 5/7275; G06N 20/00
 See application file for complete search history.

(56) References Cited

FOREIGN PATENT DOCUMENTS

| KR | 10-2020-0135052 | A | 12/2020 | |
| KR | 10-2222937 | B1 | 3/2021 | |
| WO | WO-2016166731 | A1 * | 10/2016 | ....... A61F 13/00055 |

OTHER PUBLICATIONS

Communication dated Sep. 12, 2024 in Korean Application No. 10-2022-0101524.

* cited by examiner

Figure 3:
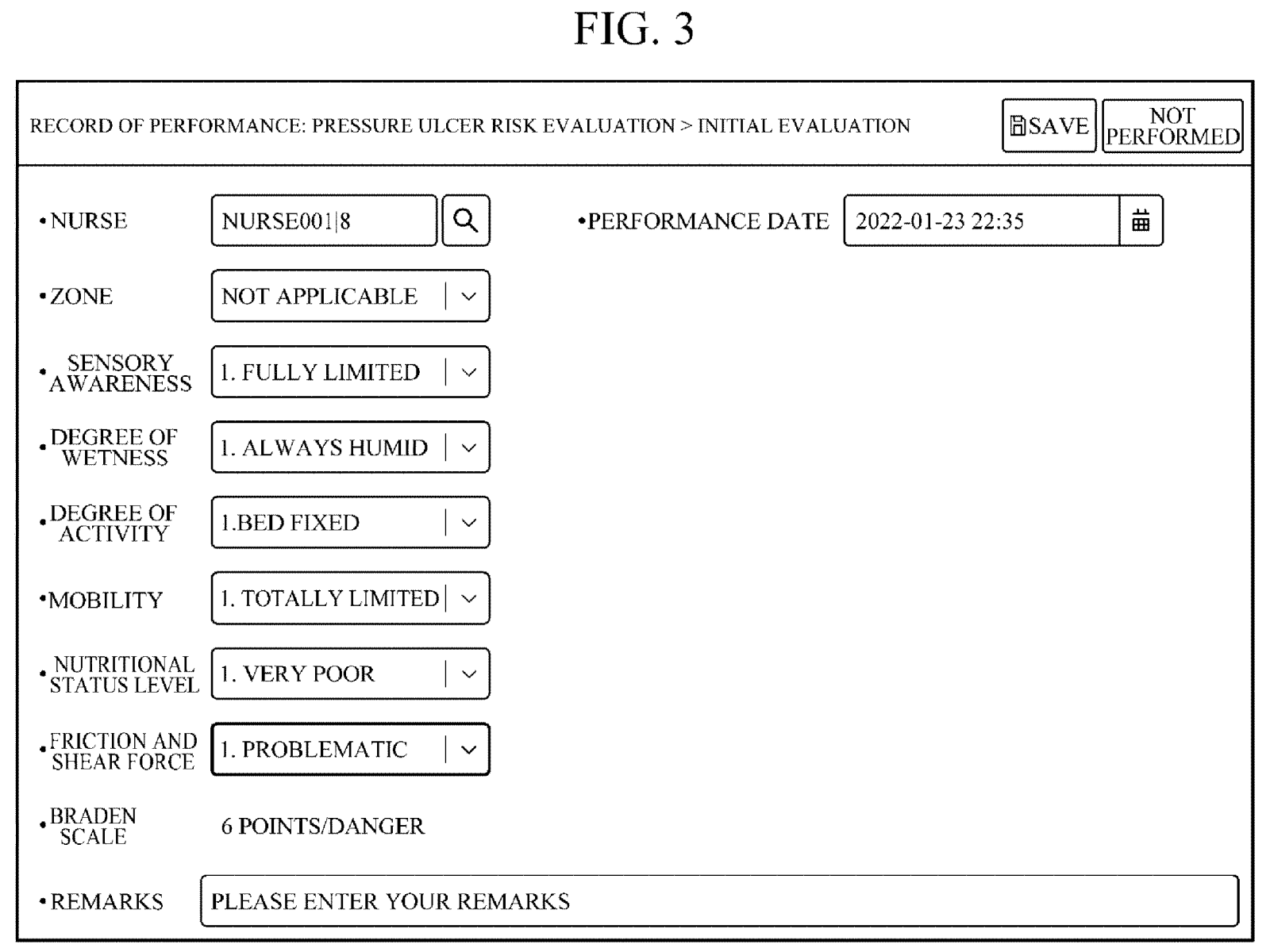

RECORD OF PERFORMANCE: PRESSURE ULCER RISK EVALUATION > INITIAL EVALUATION

🖫 SAVE    NOT PERFORMED

• PERFORMANCE DATE    2022-01-23 22:35    📅

• NURSE    NURSE0018    🔍

• ZONE    NOT APPLICABLE    ⌄

• SENSORY AWARENESS    1. FULLY LIMITED    ⌄

• DEGREE OF WETNESS    1. ALWAYS HUMID    ⌄

• DEGREE OF ACTIVITY    1.BED FIXED    ⌄

• MOBILITY    1. TOTALLY LIMITED    ⌄

• NUTRITIONAL STATUS LEVEL    1. VERY POOR    ⌄

• FRICTION AND SHEAR FORCE    1. PROBLEMATIC    ⌄

• BRADEN SCALE    6 POINTS/DANGER

• REMARKS    PLEASE ENTER YOUR REMARKS

Figure 6:
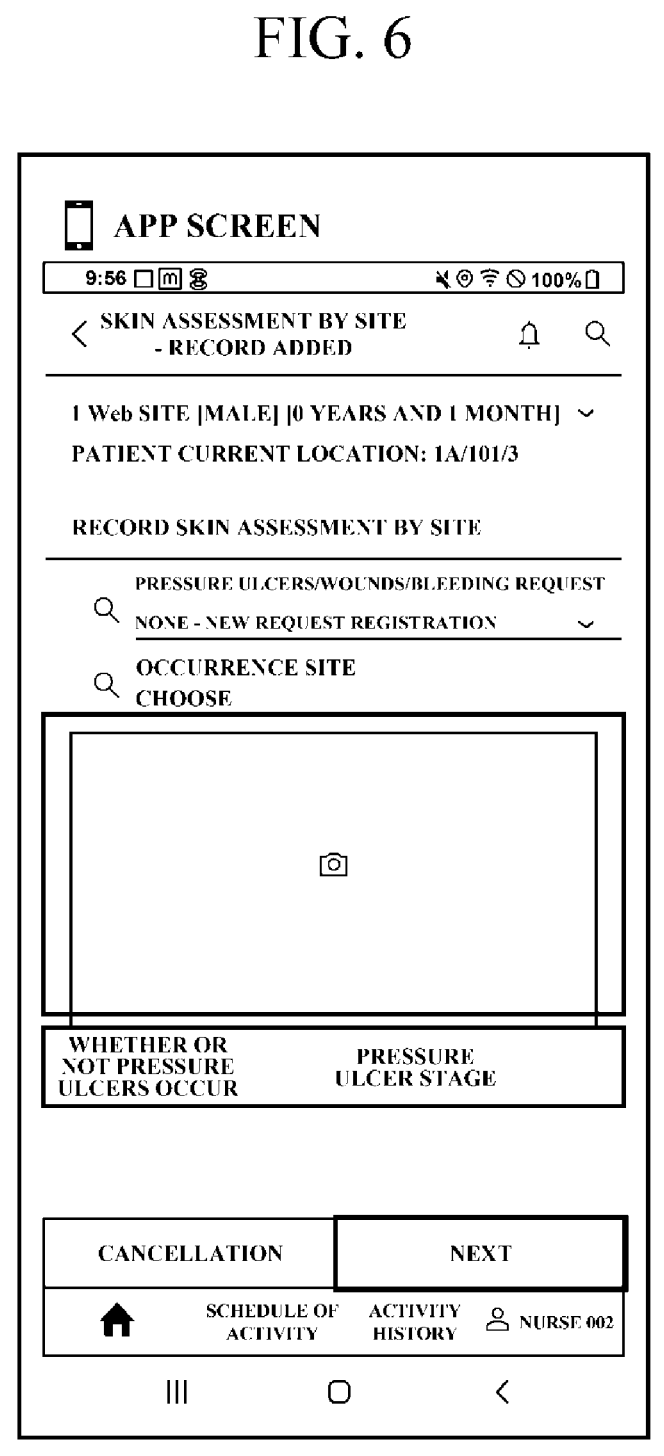

📱 APP SCREEN

9:56 □ m 🗑     ✈ ⊚ 🛜 ⊘ 100%🔋

< SKIN ASSESSMENT BY SITE - RECORD ADDED     🔔   🔍

1 Web SITE [MALE] [0 YEARS AND 1 MONTH] ∨

PATIENT CURRENT LOCATION: 1A/101/3

RECORD SKIN ASSESSMENT BY SITE

🔍   PRESSURE ULCERS/WOUNDS/BLEEDING REQUEST

NONE - NEW REQUEST REGISTRATION     ∨

🔍   OCCURRENCE SITE CHOOSE

📷

| WHETHER OR NOT PRESSURE ULCERS OCCUR | PRESSURE ULCER STAGE |
|---|---|

| CANCELLATION | NEXT |
|---|---|

🏠    SCHEDULE OF ACTIVITY    ACTIVITY HISTORY   👤 NURSE 002

|||     ○     <

METHOD AND SYSTEM FOR MANAGING PRESSURE ULCERS AND COMPUTING DEVICE FOR EXECUTING THE SAME

CROSS-REFERENCE TO RELATED APPLICATION

This application claims the benefit under 35 USC § 119(a) of Korean Patent Application No. 10-2022-0101524, filed on Aug. 12, 2022, in the Korean Intellectual Property Office, the entire disclosure of which is incorporated herein by reference for all purposes.

BACKGROUND

1. Field

Embodiments of the present disclosure relate to a technology for managing pressure ulcers.

2. Description of Related Art

The pressure ulcers refer to a condition in which pressure or a combination of pressure and friction force causes local damage to the skin in bony protruding part (e.g., sacrum, heel, etc.) of the body and its underlying tissues. Conventionally, since management of pressure ulcers relies on handwritten records of medical personnel, there is a problem in that continuous management is difficult when the medical personnel managing a corresponding patient is changed.

In addition, since training of new nurses, retraining due to job turnover, etc. frequently occur in the actual medical field, in order to maintain a low occurrence rate of pressure ulcers, it relies on the efforts of the person in charge of pressure ulcers, which results in an increase in the workload of medical staff. In addition, due to limitations in handwritten records, there are cases in which nursing interventions are omitted due to work shifts, etc.

PRIOR ART LITERATURE

Patent Literature (PTL 1) Korean unexamined patent application publication No. 10-2020-0134702 (2020.12.02)

SUMMARY

Embodiments of the present disclosure are to provide a method and system for managing pressure ulcers and a computing device for executing the same.

According to an exemplary embodiment of the present disclosure, there is provided a computing device provided with one or more processors and a memory storing one or more programs executed by the one or more processors, the computing device including a pressure ulcer risk level evaluation module configured to acquire pressure ulcer risk factor information of a patient admitted to a hospital and calculate a pressure ulcer risk level of the corresponding patient based on the acquired pressure ulcer risk factor information, and a pressure ulcer prevention management module configured to schedule a pressure ulcer prevention activity for a patient whose pressure ulcer risk level is equal to or higher than a predetermined threshold level.

The pressure ulcer risk level evaluation module may be configured to schedule a pressure ulcer risk re-evaluation time point according to the pressure ulcer risk level for each patient, and transmit a pressure ulcer risk re-evaluation notification to a medical personnel terminal in charge of the corresponding patient by checking the scheduled pressure ulcer risk re-evaluation time point.

The pressure ulcer risk level evaluation module may be configured to schedule a pressure ulcer risk re-evaluation time point according to a preset state change event of each patient, and transmit a pressure ulcer risk re-evaluation notification to a medical personnel terminal in charge of the corresponding patient by checking the scheduled pressure ulcer risk re-evaluation time point.

The pressure ulcer prevention management module may be configured to schedule the pressure ulcer prevention activity differently according to the pressure ulcer risk level of the patient.

The pressure ulcer prevention activity may include a first type pressure ulcer prevention activity and a second type pressure ulcer prevention activity, and the pressure ulcer prevention management module may be configured to transmit content for pressure ulcer prevention education to a patient-related terminal of the corresponding patient when a patient's scheduled pressure ulcer prevention activity is a first type of pressure ulcer prevention activity.

The pressure ulcer prevention management module may be configured to receive feedback on the first type of pressure ulcer prevention activity from the patient-related terminal, and calculate a first pressure ulcer prevention index of the corresponding patient based on the feedback on the first type of pressure ulcer prevention activity.

The pressure ulcer prevention management module may be configured to transmit a pressure ulcer prevention activity notification to a medical personnel terminal in charge of the corresponding patient when the patient's scheduled pressure ulcer prevention activity is a second type of pressure ulcer prevention activity.

The pressure ulcer prevention management module may be configured to receive feedback on the second type of pressure ulcer prevention activity from the medical personnel terminal, and calculate a second pressure ulcer prevention index of the corresponding patient based on the feedback on the second type of pressure ulcer prevention activity.

The pressure ulcer prevention management module may be configured to calculate a final pressure ulcer prevention index for each patient based on the first pressure ulcer prevention index and the second pressure ulcer prevention index.

The pressure ulcer risk level evaluation module may be configured to schedule a pressure ulcer re-evaluation time point according to the pressure ulcer risk level of each patient or a predetermined state change event of each patient, and perform pressure ulcer risk re-evaluation for each patient in consideration of the final pressure ulcer prevention index.

The pressure ulcer risk level evaluation module may be configured to perform the pressure ulcer risk re-evaluation by assigning a first weight to the pressure ulcer risk factor information of each patient and assigning a second weight to the final pressure ulcer prevention index of each patient.

The pressure ulcer prevention management module may be configured to transmit content related to pressure ulcer prevention education to a patient-related terminal of the corresponding patient according to a type of a patient's scheduled pressure ulcer prevention activity, or transmit a pressure ulcer prevention activity notification to a medical personnel terminal in charge of the corresponding patient.

The pressure ulcer prevention management module may be configured to calculate a pressure ulcer prevention index of the corresponding patient based on at least one of feedback on the pressure ulcer prevention activity received from the patient-related terminal and feedback on the pressure ulcer prevention activity received from the medical personnel terminal.

The pressure ulcer risk level evaluation module may be configured to schedule a pressure ulcer re-evaluation time point according to the pressure ulcer risk level of each patient or a predetermined state change event of each patient, and perform pressure ulcer risk re-evaluation for each patient in consideration of the pressure ulcer prevention index.

The computing device may further include a pressure ulcer treatment management module configured to check whether or not pressure ulcers have occurred based on an image obtained by photographing a patient's skin and configured to perform pressure ulcer treatment management of a patient with the pressure ulcers.

The pressure ulcer treatment management module may be configured to schedule a pressure ulcer treatment activity according to a degree of pressure ulcers of the patient with the pressure ulcers, and transmit a pressure ulcer treatment activity notification to a medical personnel terminal of the corresponding patient according to a set schedule.

According to another exemplary embodiment of the present disclosure, there is provided a system for managing pressure ulcers, the system including a medical personnel terminal configured to transmit pressure ulcer risk factor information of a patient admitted to a hospital, and a management server configured to receive the pressure ulcer risk factor information of the patient, calculate a pressure ulcer risk level of the corresponding patient based on the pressure ulcer risk factor information, and schedule a pressure ulcer prevention activity for a patient whose pressure ulcer risk level is equal to or higher than a predetermined threshold level.

According to still another exemplary embodiment of the present disclosure, there is provided a method for managing pressure ulcers performed in a computing device provided with one or more processors and a memory storing one or more programs executed by the one or more processors, the method including acquiring pressure ulcer risk factor information of a patient admitted to a hospital, calculating a pressure ulcer risk level of the patient based on the acquired pressure ulcer risk factor information, and scheduling a pressure ulcer prevention activity for a patient whose pressure ulcer risk level is equal to or higher than a predetermined threshold level.

According to a disclosed embodiment, by performing a pressure ulcer risk evaluation for a patient admitted to a hospital to automatically schedule a pressure ulcer prevention activity for a patient whose pressure ulcer risk level is greater than or equal to a critical level and performing a pressure ulcer prevention activity notification according to a set schedule, it is possible to continuously manage whether or not pressure ulcers occur for the hospital inpatients, thereby reducing the occurrence rate of pressure ulcers and reducing the workload of medical personnel in charge of patients. In addition, since patient's pressure ulcer-related information is automatically managed, it is possible to prevent records from being omitted.

BRIEF DESCRIPTION OF THE DRAWINGS

FIG. 3 is a view illustrating an interface for inputting pressure ulcer risk factor information of a patient in a medical personnel terminal according to an embodiment of the present disclosure.

FIG. 5 is a view illustrating a pressure ulcer prevention activity notification displayed on the medical personnel terminal according to an embodiment of the present disclosure.

FIG. 6 is a view illustrating an interface for transmitting an image obtained by photographing a patient's skin to the management server and for checking whether or not the pressure ulcers are present and a pressure ulcer stage in the medical personnel terminal according to an embodiment of the present disclosure.

DETAILED DESCRIPTION

Hereinafter, a specific embodiment of the present disclosure will be described with reference to the drawings. The following detailed description is provided to aid in a comprehensive understanding of the methods, apparatus and/or systems described herein. However, this is illustrative only, and the present disclosure is not limited thereto.

In describing the embodiments of the present disclosure, when it is determined that a detailed description of related known technologies may unnecessarily obscure the subject matter of the present disclosure, a detailed description thereof will be omitted. In addition, terms to be described later are terms defined in consideration of functions in the present disclosure, which may vary according to the intention or custom of users or operators. Therefore, the definition should be made based on the contents throughout this specification. The terms used in the detailed description are only for describing embodiments of the present disclosure, and should not be limiting. Unless explicitly used otherwise, expressions in the singular form include the meaning of the plural form. In this description, expressions such as "comprising" or "including" are intended to refer to certain features, numbers, steps, actions, elements, some or combination thereof, and it is not to be construed to exclude the presence or possibility of one or more other features, numbers, steps, actions, elements, some or combinations thereof, other than those described.

Further, terms such as first, second, etc., may be used to describe various components, but the components are not limited by the terms. The above terms may be used for the purpose of distinguishing one component from another. For example, a first component may be termed a second component, and similarly, a second component may be termed a first component, without departing from the scope of the present disclosure.

Figure 1:
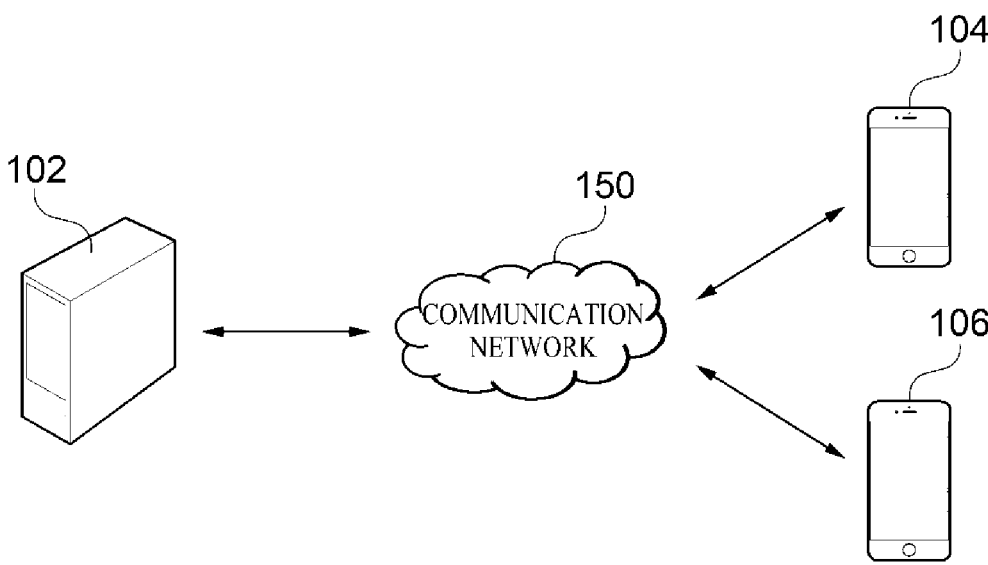
FIG. 1 is a diagram illustrating a configuration of a system for managing pressure ulcers according to an embodiment of the present disclosure.

FIG. 1 is a diagram illustrating a configuration of a pressure ulcer management system according to an embodiment of the present disclosure.

Referring to FIG. 1, a pressure ulcer management system 100 may include a management server 102, a medical personnel terminal 104, and a patient-related terminal 106.

Here, the medical personnel terminal 104 may be a terminal of medical personnel (e.g., a doctor or a nurse) in charge of a patient. The patient-related terminal 106 may be a terminal possessed by the patient or a guardian of the patient. The medical personnel terminal 104 and the patient-related terminal 106 may be a portable smart phone or tablet PC, but are not limited thereto.

The management server 102 is connected to the medical personnel terminal 104 and the patient-related terminal 106 to be able to communicate with each other through a communication network 150. In the disclosed embodiment, the communication network 150 may include the Internet, one or more local area networks, wide area networks, cellular networks, mobile networks, other types of networks, or a combination of such networks.

The management server 102 may perform pressure ulcer management for patients admitted to a hospital. The management server 102 may provide pressure ulcer risk evaluation, pressure ulcer prevention management, and pressure ulcer treatment management services of the patient.

Figure 2:
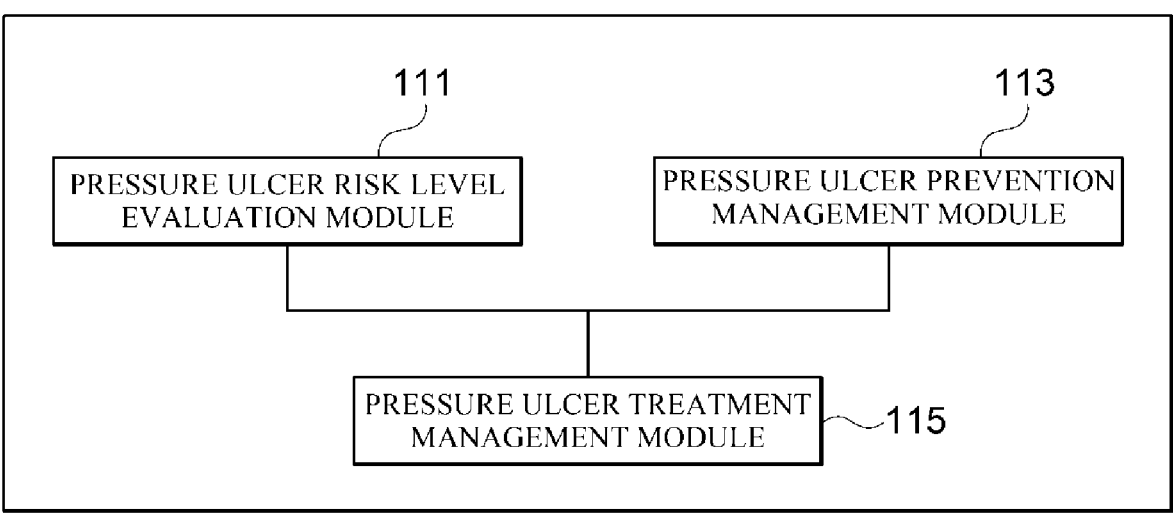
FIG. 2 is a block diagram illustrating a configuration of a management server 102 according to an embodiment of the present disclosure.

FIG. 2 is a block diagram illustrating a configuration of the management server 102 according to an embodiment of the present disclosure. Referring to FIG. 2, the management server 102 may include a pressure ulcer risk level evaluation module 111, a pressure ulcer prevention management module 113, and a pressure ulcer treatment management module 115.

The pressure ulcer risk level evaluation module 111 may perform a pressure ulcer risk evaluation targeted for the patients admitted to a hospital. The pressure ulcer risk level evaluation module 111 may acquire pressure ulcer risk factor information of each patient and calculate a pressure ulcer risk level of the corresponding patient based on the acquired pressure ulcer risk factor information. Here, the pressure ulcer risk factor information may include the sensory awareness, degree of wetness, degree of activity, degree of mobility, nutritional status level, and degree of friction and shearing force of the corresponding patient.

The sensory awareness may indicate the degree of response to a pain stimulus of the corresponding patient. The degree of wetness may indicate a degree to which the patient's skin is wet (how many times the skin is wet during a certain period of time). The degree of activity may indicate the degree and number of times the corresponding patient can walk. The degree of mobility may indicate the degree to which the corresponding patient can change his/her posture by himself/herself. The nutritional status level may indicate how much the patient has consumed the food provided to him or her. The degree of friction and shear force may indicate whether or not the corresponding patient has a friction part when moving on the bed and how much help of others is needed.

In an exemplary embodiment, the pressure ulcer risk level evaluation module 111 may classify the pressure ulcer risk level of the corresponding patient by inputting pressure ulcer risk factor information of the patient (sensory awareness, degree of wetness, degree of activity, degree of mobility, nutritional status level, degree of friction and shearing force of the corresponding patient) into a pre-trained deep learning model, but is not limited thereto. The pressure ulcer risk level evaluation module 111 may calculate the pressure ulcer risk level of the corresponding patient by assigning scores to each pressure ulcer risk factor information of the patient.

The pressure ulcer risk level evaluation module 111 may transmit a pressure ulcer risk level of each patient to the medical personnel terminal 104 in charge of the patient. In addition, the pressure ulcer risk level evaluation module 111 may transmit the pressure ulcer risk level of each patient to the patient-related terminal 106.

The pressure ulcer risk level evaluation module 111 may perform a pressure ulcer risk re-evaluation notification according to the pressure ulcer risk level for each patient. That is, the pressure ulcer risk level evaluation module 111 may schedule a pressure ulcer risk re-evaluation time point of each patient according to the pressure ulcer risk level. For example, when the pressure ulcer risk level of the patient is a preset first risk level, the pressure ulcer risk level evaluation module 111 may schedule the pressure ulcer risk re-evaluation time point of the patient to be once a week. The pressure ulcer risk level evaluation module 111 may schedule the pressure ulcer risk re-evaluation time point of the patient to be once a day when the pressure ulcer risk level of the patient is a second risk level higher than the first risk level.

The pressure ulcer risk level evaluation module 111 may check the pressure ulcer risk re-evaluation time point scheduled for each patient and transmit the pressure ulcer risk re-evaluation notification to the medical personnel terminal 104 in charge of the patient.

In addition, the pressure ulcer risk level evaluation module 111 may schedule the pressure ulcer risk re-evaluation time point according to a patient's pre-set state change event. For example, when the patient's state change event occurs, such as a change in the patient's consciousness, a change in the patient's senses, or a patient's surgery performance, the pressure ulcer risk level evaluation module 111 may schedule the pressure ulcer risk re-evaluation time point of the corresponding patient, and transmit the pressure ulcer risk re-evaluation notification to the medical personnel terminal 104 in charge of the patient at the scheduled time point.

The pressure ulcer prevention management module 113 may perform the pressure ulcer prevention management targeting a patient whose pressure ulcer risk level is equal to or higher than a predetermined threshold level (hereinafter, referred to as a pressure ulcer prevention management patient) (patient at the first risk level or second risk level and patient who needs attention due to the possibility of pressure ulcers or patient who is highly likely to develop pressure ulcers).

The pressure ulcer prevention management module 113 may schedule an activity for preventing pressure ulcers (pressure ulcer prevention activity) targeting the patient under the pressure ulcer prevention and management. The pressure ulcer prevention management module 113 may differently schedule activities for preventing pressure ulcers for a targeted patient according to the pressure ulcer risk level of the patient under the pressure ulcer prevention and management.

Here, the activity for preventing pressure ulcers may include a first type of pressure ulcer prevention activity and a second type of pressure ulcer prevention activity. The first type of pressure ulcer prevention activity is performed with the patient actively participating, and may include pressure ulcer prevention education (e.g., education on the necessity of preventing pressure ulcers, method of preventing pressure ulcers, etc.). The second type of pressure ulcer prevention activity is performed by medical personnel on a patient, and may include checking the patient's skin condition, changing the patient's body position, applying a dressing to the patient's skin, and applying moisturizers and protective agents to the patient's skin, etc.

In this time, a performance cycle or the number of times may be set for each activity for preventing pressure ulcers.

For example, pressure ulcer prevention education, checking of the patient's skin condition, application of a dressing to the patient's skin, etc. may be performed once per work cycle of the medical personnel in charge. The patient's position change may be performed once every 2 hours (position change in lying position) or 15 minutes (position change in sitting position) depending on the patient's positional condition.

The pressure ulcer prevention management module 113 may perform a pressure ulcer prevention activity notification for each patient. Specifically, when the patient's scheduled pressure ulcer prevention activity is the first type of pressure ulcer prevention activity, the pressure ulcer prevention management module 113 may transmit content related to the pressure ulcer prevention education (e.g., content that explains the necessity of preventing pressure ulcers or content that explains the method of preventing pressure ulcers, etc.) to the patient-related terminal 106 of the corresponding patient.

The pressure ulcer prevention management module 113 may receive feedback on the first type of pressure ulcer prevention activity from the patient-related terminal 106. The feedback on the pressure ulcer prevention activity of the first type may be how much a patient or a guardian of the patient watched and understood the content on the pressure ulcer prevention education. The pressure ulcer prevention management module 113 may calculate a first pressure ulcer prevention index of the patient based on the feedback on the first type of pressure ulcer prevention activity.

In addition, when the patient's scheduled pressure ulcer prevention activity is the second type of pressure ulcer prevention activity, the pressure ulcer prevention management module 113 may transmit the pressure ulcer prevention activity notification to the medical personnel terminal 104 in charge of the corresponding patient. In this case, the pressure ulcer prevention activity notification may include the type and time of the second type of pressure ulcer prevention activity.

Here, although it has been described that the pressure ulcer prevention management module 113 transmits the pressure ulcer prevention activity notification to the medical personnel terminal 104, but is not limited thereto, and the medical personnel terminal 104 may access the management server 102 to check the pressure ulcer prevention activity for each patient.

The pressure ulcer prevention management module 113 may receive feedback on the second type of pressure ulcer prevention activity from the medical personnel terminal 104. The feedback on the second type of pressure ulcer prevention activity may be whether each pressure ulcer prevention activity has been properly performed, whether or not the pressure ulcer prevention activity has been delayed, and if so, to what extent the pressure ulcer prevention activity has been delayed. The pressure ulcer prevention management module 113 may calculate a second pressure ulcer prevention index of the patient based on the feedback on the pressure ulcer prevention activity.

The pressure ulcer prevention management module 113 may calculate a final pressure ulcer prevention index by summing the first pressure ulcer prevention index and the second pressure ulcer prevention index for each patient. The final pressure ulcer prevention index for each patient may be reflected when performing a pressure ulcer risk re-evaluation for the patient. That is, the pressure ulcer risk level evaluation module 111 may perform the pressure ulcer risk re-evaluation) by considering not only the pressure ulcer risk factor information of the patient but also the final pressure ulcer prevention index. In an exemplary embodiment, the pressure ulcer risk level evaluation module 111 may recalculate pressure ulcer risk level of the patient by assigning a first weight to the pressure ulcer risk factor information of the patient and assigning a second weight to the final pressure ulcer prevention index of the patient. Here, the second weight may be given a smaller value than the first weight. That is, the final pressure ulcer prevention index of the patient may be intended to supplement or assist the pressure ulcer risk factor information of the patient so as to re-evaluate the pressure ulcer risk level of the patient.

The pressure ulcer treatment management module 115 may check whether or not the pressure ulcers have occurred based on an image obtained by photographing the patient's skin. Specifically, the pressure ulcer treatment management module 115 may acquire an image of the patient's skin (skin in areas having a high risk of pressure ulcers). The image obtained by photographing the patient's skin may be acquired from the medical personnel terminal 104. For example, the medical personnel terminal 104 may photograph the patient's skin in checking the patient's skin condition or changing the patient's position change during the second type of pressure ulcer prevention activity, and transmit the photographed image to the management server 102.

In an exemplary embodiment, the pressure ulcer treatment management module 115 may input the image obtained by photographing the patient's skin to the pre-trained deep learning model to check whether or not the pressure ulcers have occurred and, if the pressure ulcers occur, to determine the degree of pressure ulcers.

The pressure ulcer treatment management module 115 may perform pressure ulcers treatment management of a patient with pressure ulcers. The pressure ulcer treatment management module 115 may schedule the pressure ulcer treatment activity depending on the degree of pressure ulcers. The pressure ulcer treatment management module 115 may perform a pressure ulcer treatment activity notification according to a set schedule. The pressure ulcer treatment management module 115 may transmit the pressure ulcer treatment activity notification to the medical personnel terminal 104 of the corresponding patient. The pressure ulcer treatment activity notification may include the type and time of the pressure ulcer treatment activity.

According to the disclosed embodiment, by performing the pressure ulcer risk evaluation for the patient admitted to a hospital to automatically schedule the pressure ulcer prevention activity for the patient whose pressure ulcer risk level is greater than or equal to a critical level and performing the pressure ulcer prevention activity notification according to the set schedule, it is possible to continuously manage whether or not the pressure ulcers occur, thereby reducing the occurrence rate of pressure ulcers and reducing the workload of medical personnel in charge of patients. In addition, since patient's pressure ulcer-related information is automatically managed, it is possible to prevent records from being omitted.

In other words, as pressure ulcer risk evaluation, pressure ulcer prevention activity management, pressure ulcer treatment activity management, etc. are datafied, scheduled, and notified through the management server, omission of records related to pressure ulcers of patients can be prevented, the occurrence rate of pressure ulcers can be reduced by continuously managing the patient, and the workload of medical personnel in charge can be reduced.)

In this specification, a module may mean a functional and structural combination of hardware for implementing the technical idea of the present disclosure and software for driving the hardware. For example, the "module" may mean a logical unit of predetermined codes and hardware resources for executing the predetermined codes, and does not necessarily mean physically connected codes or one type of hardware.

Meanwhile, the medical personnel terminal 104 may provide pressure ulcer risk evaluation, pressure ulcer prevention management, and pressure ulcer treatment management services in conjunction with the management server 102. To this end, a predetermined application may be installed in the medical personnel terminal 104.

The application may be stored in a computer readable storage medium of the medical personnel terminal 104. The application includes a predetermined set of instructions executable by a processor of the medical personnel terminal 104. The instructions may cause the processor of the medical personnel terminal 104 to perform an operation according to an exemplary embodiment. The computer readable storage medium of the medical personnel terminal 104 includes components of an operating system for executing a set of instructions such as the application on the medical personnel terminal 104. For example, such an operating system may be Apple's iOS or Google's Android.

For example, as illustrated in FIG. 3, the medical personnel terminal 104 may receive pressure ulcer risk factor information of a patient admitted to a hospital (sensory awareness, degree of wetness, degree of activity, degree of mobility, nutritional status level, and degree of friction and shearing force of the corresponding patient) as input and transmit the pressure ulcer risk factor information to the management server 102.

Figure 4:
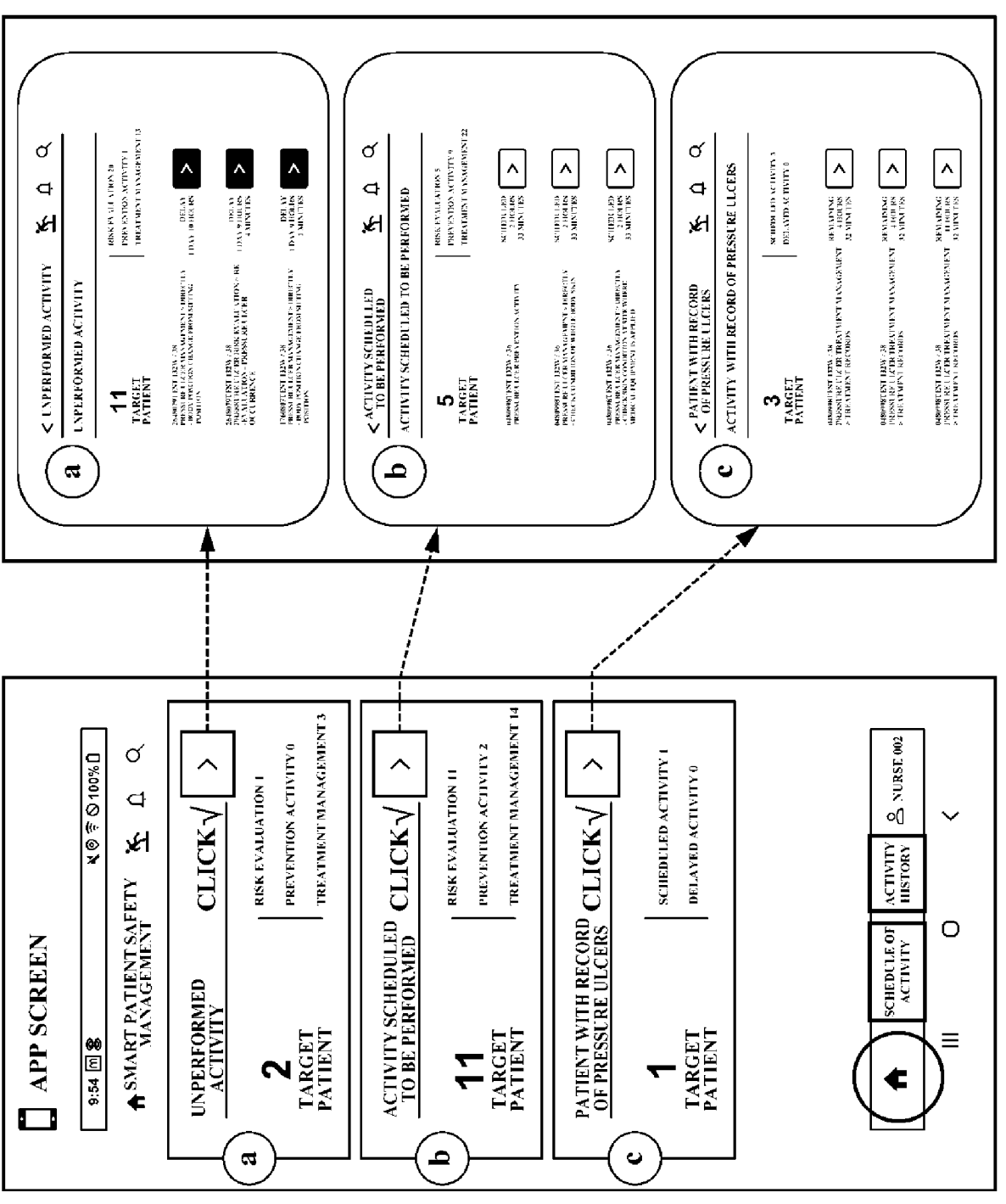
FIG. 4 is a view illustrating a state in which a schedule related to pressure ulcers is checked in the medical personnel terminal according to an embodiment of the present disclosure.

In addition, as illustrated in FIG. 4, the medical personnel terminal 104 may check pressure ulcer risk re-evaluation, pressure ulcer prevention activity, pressure ulcer treatment activity schedule, etc. of the patients through the application. In this case, the management server 102 may provide the medical personnel terminal 104 with information on the patients who are not subjected to the pressure ulcer prevention activity and the pressure ulcer treatment activity (activities not performed) according to each schedule and information on a patient who should be subjected to the pressure ulcer prevention activity and the pressure ulcer treatment activity (activities to be performed) according to each schedule.

Figure 5:
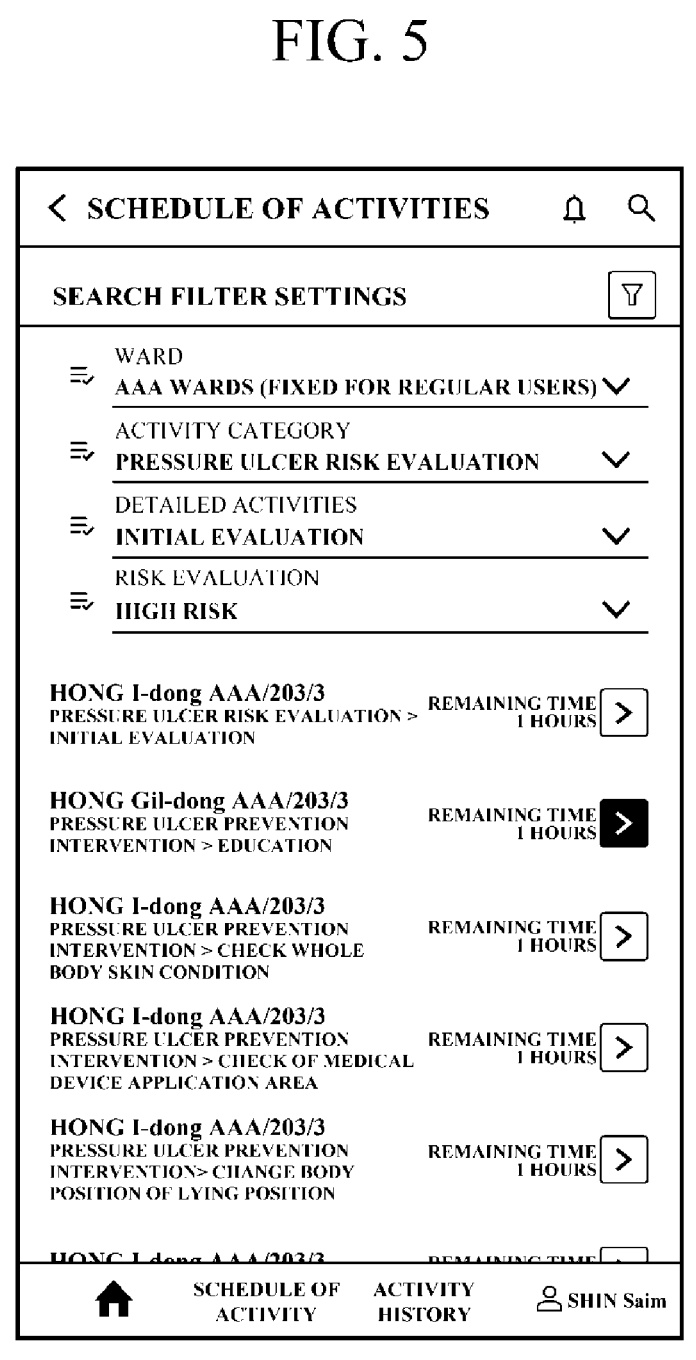

FIG. 5 is a diagram illustrating the pressure ulcer prevention activity notification displayed on the medical personnel terminal 104 according to an embodiment of the present disclosure. Referring to FIG. 5, the pressure ulcer prevention activity notification (types and times of pressure ulcer prevention activities) may be displayed on the medical personnel terminal 104 for each patient in charge of the corresponding medical personnel.

In addition, as illustrated in FIG. 6, the medical personnel terminal 104 may be provided with an interface for transmitting the image obtained by photographing the patient's skin to the management server 102 and for receiving and checking whether or not pressure ulcers are present and the level of pressure ulcers from the management server 102.

Figure 7:
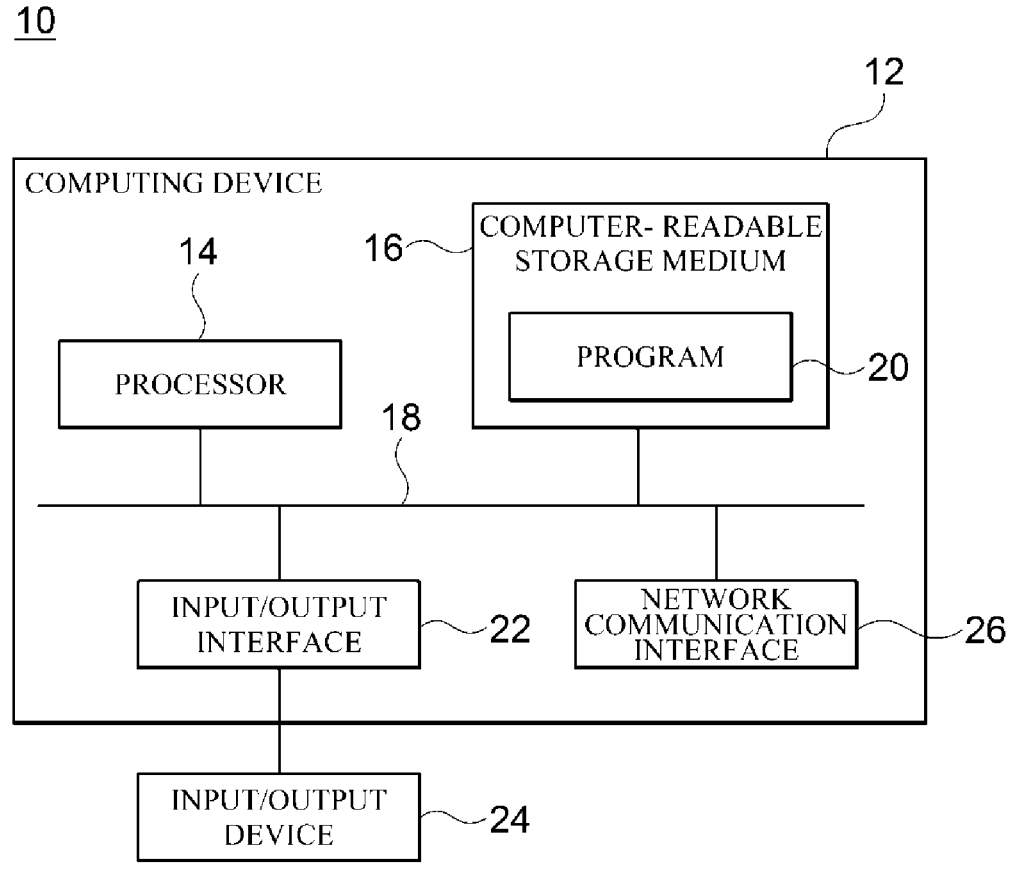
FIG. 7 is a block diagram for illustratively describing a computing environment including a computing device suitable for use in exemplary embodiments.

FIG. 7 is a block diagram for illustratively describing a computing environment 10 including a computing device suitable for use in exemplary embodiments. In the illustrated embodiment, respective components may have different functions and capabilities other than those described below, and may include additional components in addition to those described below.

The illustrated computing environment 10 includes a computing device 12. In an embodiment, the computing device 12 may be the be management server 102. In addition, the computing device 12 may be the medical personnel terminal 104.

The computing device 12 includes at least one processor 14, a computer-readable storage medium 16, and a communication bus 18. The processor 14 may cause the computing device 12 to operate according to the exemplary embodiment described above. For example, the processor 14 may execute one or more programs stored on the computer-readable storage medium 16. The one or more programs may include one or more computer-executable instructions, which, when executed by the processor 14, may be configured so that the computing device 12 performs operations according to the exemplary embodiment.

The computer-readable storage medium 16 is configured so that the computer-executable instruction or program code, program data, and/or other suitable forms of information are stored. A program 20 stored in the computer-readable storage medium 16 includes a set of instructions executable by the processor 14. In one embodiment, the computer-readable storage medium 16 may be a memory (volatile memory such as a random access memory, non-volatile memory, or any suitable combination thereof), one or more magnetic disk storage devices, optical disk storage devices, flash memory devices, other types of storage media that are accessible by the computing device 12 and capable of storing desired information, or any suitable combination thereof.

The communication bus 18 interconnects various other components of the computing device 12, including the processor 14 and the computer-readable storage medium 16.

The computing device 12 may also include one or more input/output interfaces 22 that provide an interface for one or more input/output devices 24, and one or more network communication interfaces 26. The input/output interface 22 and the network communication interface 26 are connected to the communication bus 18. The input/output device 24 may be connected to other components of the computing device 12 through the input/output interface 22. The exemplary input/output device 24 may include a pointing device (such as a mouse or trackpad), a keyboard, a touch input device (such as a touch pad or touch screen), a speech or sound input device, input devices such as various types of sensor devices and/or photographing devices, and/or output devices such as a display device, a printer, a speaker, and/or a network card. The exemplary input/output device 24 may be included inside the computing device 12 as a component configuring the computing device 12, or may be connected to the computing device 12 as a separate device distinct from the computing device 12.

Although representative embodiments of the present disclosure have been described in detail, a person skilled in the art to which the present disclosure pertains will understand that various modifications may be made thereto within the limits that do not depart from the scope of the present disclosure. Therefore, the scope of rights of the present disclosure should not be limited to the described embodiments, but should be defined not only by claims set forth below but also by equivalents to the claims.

What is claimed is:

1. A computing device comprising one or more processors and a memory storing one or more programs executed by the one or more processors, wherein the one or more processors are configured to execute the one or more programs to: acquire pressure ulcer risk factor information of a patient admitted to a hospital and acquire a pressure ulcer risk level of the patient by inputting the acquired pressure ulcer risk factor information into a pre-trained deep learning model, wherein the pressure ulcer risk factor information of the patient includes sensory awareness, degree of wetness, degree of activity, degree of mobility, nutritional status level, degree of friction and shearing force of the patient; and automatically schedule a pressure ulcer prevention activity for the patient when the pressure ulcer risk level is equal to or higher than a predetermined threshold level, wherein the one or more processors are further configured to execute the one or more programs to:

based on a type of the pressure ulcer prevention activity for the patient, transmit content related to pressure ulcer prevention education to a patient-related terminal of the patient or transmit a pressure ulcer prevention activity notification to a medical personnel terminal in charge of the patient, and calculate a pressure ulcer prevention index of the patient based on at least one of feedback on the pressure ulcer prevention activity received from the patient-related terminal and feedback on the pressure ulcer prevention activity received from the medical personnel terminal.

2. The computing device of claim 1, wherein the one or more processors are further configured to execute the one or more programs to schedule a pressure ulcer risk re-evaluation time point according to the pressure ulcer risk level of the patient, and transmit a pressure ulcer risk re-evaluation notification to the medical personnel terminal in charge of the patient by checking the scheduled pressure ulcer risk re-evaluation time point.

3. The computing device of claim 1, wherein the one or more processors are further configured to execute the one or more programs to schedule a pressure ulcer risk re-evaluation time point according to a preset state change event of the patient, and transmit a pressure ulcer risk re-evaluation notification to the medical personnel terminal in charge of the patient by checking the scheduled pressure ulcer risk re-evaluation time point.

4. The computing device of claim 1, wherein the one or more processors are further configured to execute the one or more programs to schedule the pressure ulcer prevention activity differently according to the pressure ulcer risk level of the patient.

5. The computing device of claim 1, wherein the pressure ulcer prevention activity is a first type of pressure ulcer prevention activity or a second type of pressure ulcer prevention activity, and the one or more processors are further configured to execute the one or more programs to transmit the content for pressure ulcer prevention education to the patient-related terminal of the patient when the patient's scheduled pressure ulcer prevention activity is the first type of pressure ulcer prevention activity.

6. The computing device of claim 5, wherein the one or more processors are further configured to execute the one or more programs to receive feedback on the first type of pressure ulcer prevention activity from the patient-related terminal, and calculate a first pressure ulcer prevention index of the patient based on the feedback on the first type of pressure ulcer prevention activity.

7. The computing device of claim 6, wherein the one or more processors are further configured to execute the one or more programs to transmit the pressure ulcer prevention activity notification to the medical personnel terminal in charge of the patient when the patient's scheduled pressure ulcer prevention activity is the second type of pressure ulcer prevention activity.

8. The computing device of claim 7, wherein the one or more processors are further configured to execute the one or more programs to receive feedback on the second type of pressure ulcer prevention activity from the medical personnel terminal, and calculate a second pressure ulcer prevention index of the patient based on the feedback on the second type of pressure ulcer prevention activity.

9. The computing device of claim 8, wherein the one or more processors are further configured to execute the one or more programs to calculate a final pressure ulcer prevention index for the patient based on the first pressure ulcer prevention index and the second pressure ulcer prevention index.

10. The computing device of claim 9, wherein the one or more processors are further configured to execute the one or more programs to schedule a pressure ulcer re-evaluation time point according to the pressure ulcer risk level of the patient or a predetermined state change event of the patient, and perform pressure ulcer risk re-evaluation for the patient in consideration of the final pressure ulcer prevention index.

11. The computing device of claim 10, wherein the one or more processors are further configured to execute the one or more programs to perform the pressure ulcer risk re-evaluation by assigning a first weight to the pressure ulcer risk factor information of the patient and assigning a second weight to the final pressure ulcer prevention index of the patient.

12. The computing device of claim 1, wherein the one or more processors are further configured to execute the one or more programs to schedule a pressure ulcer re-evaluation time point according to the pressure ulcer risk level of the patient or a predetermined state change event of the patient, and perform pressure ulcer risk re-evaluation for the patient in consideration of the pressure ulcer prevention index.

13. The computing device of claim 1, wherein the one or more processors are further configured to execute the one or more programs to check whether or not pressure ulcers have occurred based on an image obtained by photographing the patient's skin and configured to perform pressure ulcer treatment management of the patient with the pressure ulcers.

14. The computing device of claim 13 wherein the one or more processors are further configured to execute the one or more programs to schedule a pressure ulcer treatment activity according to a degree of pressure ulcers of the patient with the pressure ulcers, and transmit a pressure ulcer treatment activity notification to the medical personnel terminal of the patient according to a set schedule.

15. A system for managing pressure ulcers, the system comprising:

a medical personnel terminal configured to transmit pressure ulcer risk factor information of a patient admitted to a hospital; and a management server configured to receive the pressure ulcer risk factor information of the patient, acquire a pressure ulcer risk level of the patient by inputting the pressure ulcer risk factor information into a pre-trained deep learning model, and automatically schedule a pressure ulcer prevention activity for the patient when the pressure ulcer risk level is equal to or higher than a predetermined threshold level, wherein the pressure ulcer risk factor information of the patient includes sensory awareness, degree of wetness, degree of activity, degree of mobility, nutritional status level, degree of friction and shearing force of the patient, wherein the management server is further configured to:

based on a type of the pressure ulcer prevention activity for the patient, transmit content related to pressure ulcer prevention education to a patient-related terminal of the patient or transmit a pressure ulcer prevention activity notification to the medical personnel terminal in charge of the patient, and calculate a pressure ulcer prevention index of the patient based on at least one of feedback on the pressure ulcer prevention activity received from the patient-related terminal and feedback on the pressure ulcer prevention activity received from the medical personnel terminal.

16. A method for managing pressure ulcers performed in a computing device including one or more processors and a memory storing one or more programs executed by the one or more processors, the method performed by the one or more processors and comprising:

acquiring pressure ulcer risk factor information of a patient admitted to a hospital;

acquiring a pressure ulcer risk level of the patient by inputting the acquired pressure ulcer risk factor information into a pre-trained deep learning model, wherein the pressure ulcer risk factor information of the patient includes sensory awareness, degree of wetness, degree of activity, degree of mobility, nutritional status level, degree of friction and shearing force of the patient; and automatically scheduling a pressure ulcer prevention activity for the patient when the pressure ulcer risk level is equal to or higher than a predetermined threshold level, wherein the method further comprises:

based on a type of the pressure ulcer prevention activity for the patient, transmitting content related to pressure ulcer prevention education to a patient-related terminal of the patient or transmitting a pressure ulcer prevention activity notification to a medical personnel terminal in charge of the patient, and calculating a pressure ulcer prevention index of the patient based on at least one of feedback on the pressure ulcer prevention activity received from the patient-related terminal and feedback on the pressure ulcer prevention activity received from the medical personnel terminal.

17. A non-transitory computer readable storage medium storing a computer program, wherein the computer program includes one or more instructions that, when executed by a computing device including one or more processors, cause the computing device to:

acquire pressure ulcer risk factor information of a patient admitted to a hospital;

acquire a pressure ulcer risk level of the patient by inputting the acquired pressure ulcer risk factor information into a pre-trained deep learning model, wherein the pressure ulcer risk factor information of the patient includes sensory awareness, degree of wetness, degree of activity, degree of mobility, nutritional status level, degree of friction and shearing force of the patient; and automatically schedule a pressure ulcer prevention activity for the patient when the pressure ulcer risk level is equal to or higher than a predetermined threshold level, wherein the one or more instructions, when executed by the computing device including the one or more processors, cause the computing device to:

based on a type of the pressure ulcer prevention activity for the patient, transmit content related to pressure ulcer prevention education to a patient-related terminal of the patient or transmit a pressure ulcer prevention activity notification to a medical personnel terminal in charge of the patient, and calculate a pressure ulcer prevention index of the patient based on at least one of feedback on the pressure ulcer prevention activity received from the patient-related terminal and feedback on the pressure ulcer prevention activity received from the medical personnel terminal.

* * * * *